(12) United States Patent
Burger et al.

(10) Patent No.: US 7,485,258 B2
(45) Date of Patent: Feb. 3, 2009

(54) METHOD AND DEVICE FOR STERILIZING CONTAINERS

(75) Inventors: Kurt Burger, Friolzheim (DE); Guenter Schneider, Besigheim (DE); Thomas Beck, Kirchberg (DE); Wolfgang Szczerba, Murrhardt (DE); Bernd Wilke, Leutenbach (DE); Johannes Rauschnabel, Stuttgart (DE); Sascha Henke, Weil der Stadt (DE); Bernd Goetzelmann, Rot Am See (DE); Heinrich Van De Loecht, Rudersberg (DE); Wolfgang Schmitt, Schorndorf (DE)

(73) Assignee: Robert Bosch GmbH, Stuttgart (DE)

( * ) Notice: Subject to any disclaimer, the term of this patent is extended or adjusted under 35 U.S.C. 154(b) by 981 days.

(21) Appl. No.: 10/398,568

(22) PCT Filed: Jul. 9, 2002

(86) PCT No.: PCT/DE02/02503

§ 371 (c)(1),
(2), (4) Date: Apr. 8, 2003

(87) PCT Pub. No.: WO03/016143

PCT Pub. Date: Feb. 27, 2003

(65) Prior Publication Data

US 2005/0019209 A1    Jan. 27, 2005

(30) Foreign Application Priority Data

Aug. 8, 2001    (DE) ................................ 101 38 938

(51) Int. Cl.
*A61L 9/00* (2006.01)
*A61L 2/00* (2006.01)
*A62B 7/08* (2006.01)
*B01J 19/08* (2006.01)
*G01N 23/00* (2006.01)
*G01N 21/00* (2006.01)
*A61N 5/00* (2006.01)
*H05F 3/00* (2006.01)
*C25D 17/00* (2006.01)

(52) U.S. Cl. .................. 422/22; 422/4; 422/5; 422/21; 422/23; 422/121; 422/186.01; 422/186.04; 422/186.05; 422/186.29; 422/292; 422/300; 422/302; 422/303; 422/304; 422/305; 422/306; 422/906; 422/907; 422/33; 250/455.11; 250/453.11; 250/492.1; 204/157.15; 204/157.44; 204/164; 204/199; 204/212; 204/213; 204/214

(58) Field of Classification Search ................. 422/4–5, 422/21–22, 121, 186.01, 186.04, 186.05, 422/186.29, 292, 300, 305–306, 906–907, 422/33; 250/455.11, 453.11, 492.1; 204/157.15, 204/157.44, 164, 199, 212–214

See application file for complete search history.

(56) References Cited

U.S. PATENT DOCUMENTS 1,804,484 A * 5/1931 Wetmore .................... 118/686

(Continued)

*Primary Examiner*—Jill Warden
*Assistant Examiner*—Monzer R Chorbaji
(74) *Attorney, Agent, or Firm*—Ronald E. Greigg

(57) ABSTRACT

A method and device for sterilizing containers in which a plasma treatment is executed through excitation of an electromagnetic oscillation so that the plasma is excited in a vacuum in the vicinity of the container regions to be sterilized. Between arrival and discharge, the container regions to be sterilized are moved closer to the oscillation-generating device in the chamber, with continuous movement of the container and/or of the oscillation-generating device for one or more predetermined time intervals in such a way that a plasma is excited in these regions inside and/or outside the container. The chamber is provided with a transport apparatus inside it, which produces an essentially rotating motion of the container during the transport from the arrival to the discharge in the chamber.

23 Claims, 5 Drawing Sheets

U.S. PATENT DOCUMENTS

| | | | | |
|---|---|---|---|---|
| 3,600,126 | A | * | 8/1971 | Hellund .................... 422/23 |
| 4,207,286 | A | * | 6/1980 | Gut Boucher ............. 422/21 |
| 5,323,442 | A | * | 6/1994 | Golovanivsky et al. ..... 378/119 |
| 5,534,231 | A | * | 7/1996 | Savas ....................... 216/67 |
| 6,223,683 | B1 | * | 5/2001 | Plester et al. ......... 118/723 VE |
| 6,230,472 | B1 | * | 5/2001 | Stahlecker ................ 53/426 |
| 6,457,299 | B1 | * | 10/2002 | Schwenke et al. ........... 53/510 |

* cited by examiner

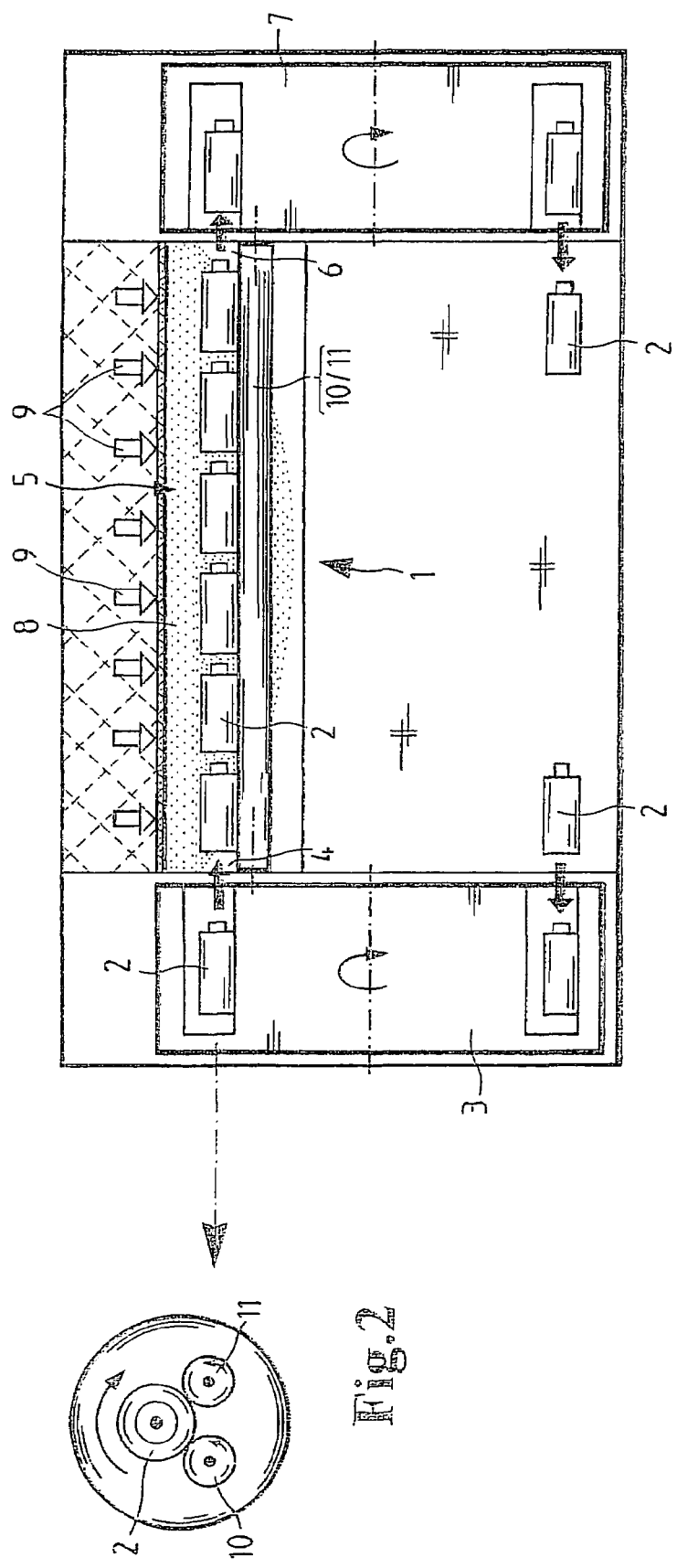

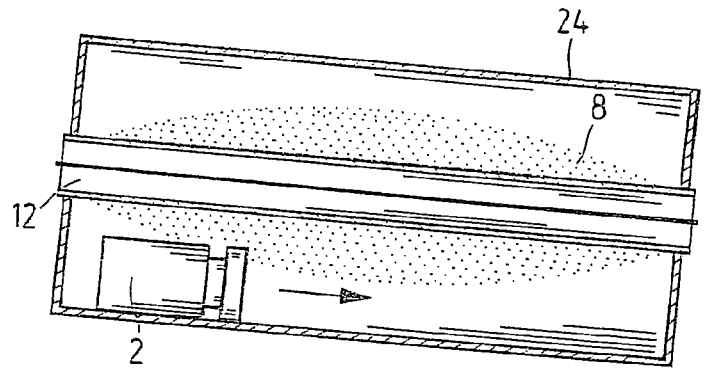
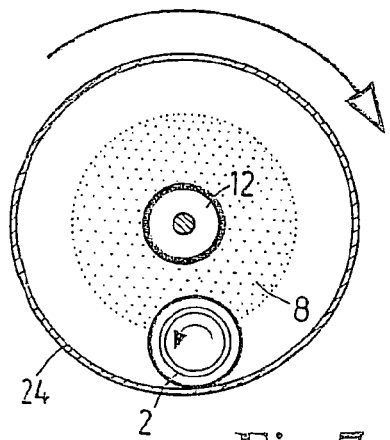
Fig.6    Fig.7
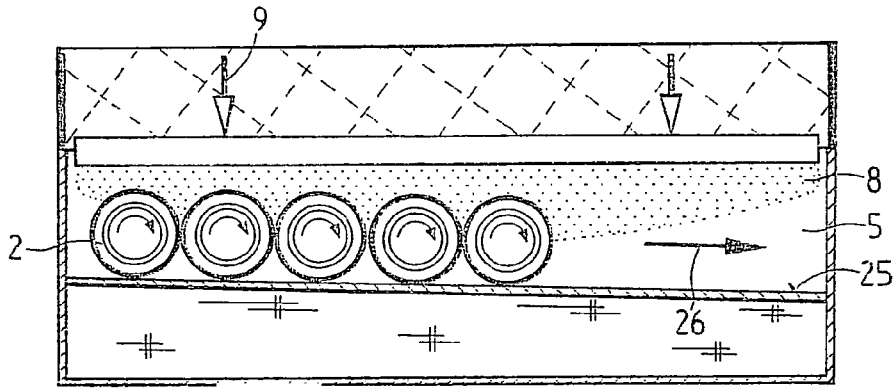
Fig.8
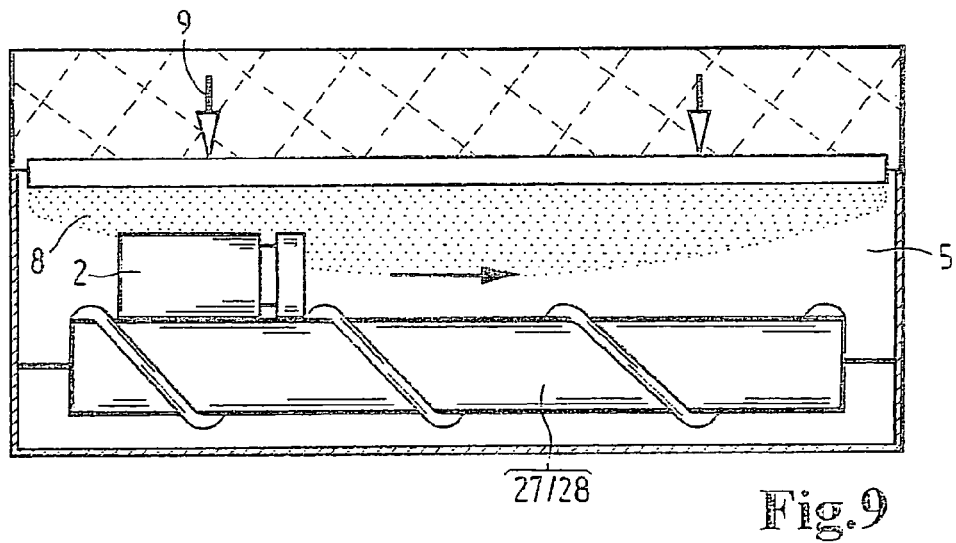
Fig.9

METHOD AND DEVICE FOR STERILIZING CONTAINERS

CROSS-REFERENCE TO RELATED APPLICATIONS

This application is a 35 USC 371 application of PCT/DE 02/02503 filed on Jul. 9, 2002.

BACKGROUND OF THE INVENTION

1. Field of the Invention The invention relates to an improved method for sterilizing containers and to improved devices for executing the method.

2. Description of the Prior Art

It is sufficiently well-known in the fields of medicine or food technology to use physical or chemical methods to remove dangerous microorganisms or germs in containers, for example in ampules, septic glass containers, syringes, vials, and other so-called parenteralia packages, or in beverage bottles.

The sterilization of devices and packaging through the use of dry heat is known, for example, from WO-9839216 A1 or EP 0512244 A1.

Furthermore, in an intrinsically known steam method with an aqueous precleaning, the containers can be subjected for a predetermined time interval to hot or superheated steam. The duration of the process requires large systems in order to be able to sterilize large numbers of articles in a manner that is integrated into the production stream. This steam sterilization, however, is not able to completely remove so-called pyrogens, i.e. inflammation-inducing decomposition products and cellular residue components of dead germs.

Both of the methods mentioned above have their own specific disadvantages. The application of dry heat requires that the devices to be treated be made of temperature-stable materials, e.g. steel, ceramic, or glass. Furthermore, the heat treatment specifically in the region to be filled with parenteralia must be immediately followed by a cooling process that is expensive, particularly with regard to energy, space, and investment costs, in order to be able to be filled with temperature-sensitive materials at room temperature.

This is why chemicals are also often used for sterilization, for example peracetic acid or hydrogen peroxide in the vapor phase, e.g. known from DE 24 35 037 A1, or gaseous ethylene oxide. A treatment, for example, with hydrogen peroxide vapor does in fact produce oxidation of dead cell residue components, but requires a careful cleaning and a correspondingly high cost. Moreover, many packaging materials, for example many plastics, are not stable in the presence of hydrogen peroxide. Up to now, it has only been possible to use these two methods with glass containers, since the required temperatures are too high for plastic containers.

In addition, methods with UV radiation, known per se from DE 25 30 113 A1, or with Gamma radiation according to WO 95 33 651 A1 have proven advantageous due to their sterilizing properties and are therefore used to sterilize articles and packaging.

EP 0 377 799 A1 has disclosed a method in which a plasma is generated using an electromagnetic radiation with a frequency of approximately 2.45 GHz in order to sterilize articles. In order to achieve this, the entire article is exposed to a low-pressure plasma and in one modification, is also irradiated by an additional heat source. Up to now, sterilization by means of a plasma has mainly been used to treat medical devices, for example catheters or transfusion instruments.

The sterilization, i.e. the degradation of viable organisms, in the known methods described above is insufficient for use on articles in the medical field, for example medical instruments or the packaging of parenteralia. These applications also require that inflammation-inducing residual components, so-called endotoxins, of the dead germs also be removed or at least permanently inactivated with regard to their pyrogenic effects. This applies primarily to so-called lipopolysaccharides of Gram-negative bacteria, which are disposed on the outside of the cell wall and, when they get into the bloodstream, can provoke defensive reactions.

The provision of a sufficient endotoxin degradation through the action of heat in this instance requires an at least 300° C. container temperature and currently only suffices if there is a long heat treatment of >5 min., which is followed by an even longer cooling phase. In the case of plasma sterilization using hydrogen peroxide, the plasma is only used to remove peroxide residues from substrates. The sterilizing action is the conventional chemical action of hydrogen peroxide. The processing times are therefore correspondingly long, i.e. as a rule greater than 30 minutes.

This plasma process consequently requires a large amount of time and the use of an aggressive chemical, for example hydrogen peroxide or peracetic acid, all residues of which must be removed before further use of the devices. Moreover, special devices are required, in order, in hollow articles, to assure a sufficient germ and endotoxin degradation on the inside of the hollow articles as well, as described, for example, in U.S. Pat. No. 5,200,158 A1.

Furthermore, the scientific paper by R. E. Peeples and N. R. Anderson in the *Journal of Parenteral Science and Technology*, Vol. 39/1, pp. 9-15, 1985 has disclosed a method in which a microwave launch can ignite a plasma in a vial for the purpose of endotoxin degradation. In this case, the plasma was ignited with the aid of a laser flash and was only maintained for a few seconds. This produced a large temperature gradient inside the vial, e.g. 31° C. at the bottom and 1665° C. at the lip. The technical complexity with the use of a microwave source and a laser as well as the unsatisfactory guarantee of ignition, particularly with different hollow body formats, and the enormous temperature gradient are disadvantageous, particularly for use in packaging technology applications.

SUMMARY OF THE INVENTION

A method for sterilizing containers or articles, in which an electromagnetic oscillation is excited in such a way that a plasma can be exited in a vacuum in the vicinity of the container regions to be sterilized, is advantageously modified according to the invention. To this end, between the arrival and discharge, the container regions to be sterilized are moved closer to the oscillation-generating device in the chamber, through movement of the container and/or the oscillation-generating device for one or more predetermined time intervals in such a way that a plasma is exited in these regions inside and/or outside the container.

The exemplary embodiments of a method according to the invention and the devices that can be produced to execute them, both of which are explained below, use the excitation of a high-frequency plasma or microwave plasma in the low-pressure region or in the vacuum, through a guidance of the containers to be treated, which are of the type mentioned at the beginning, at a definite distance from the launch of the microwave field, with a simultaneous rotation and transport of the containers along the plasma source or of a cascade of sources, in order to provide a treatment on all sides and prevention of a contact contamination. In this connection, it is particularly advantageous that all surfaces of the transport apparatus, which can come into contact with the containers, are also exposed to the plasma.

Furthermore, in a particularly advantageous manner, it is possible to assure the production of an expanded plasma zone between the container stocking (arrival) and the container removal (discharge). All articles, gases, or particles must cross through this plasma zone in order to travel from the arrival to the discharge. This assures that during the discharge, there cannot be any entrainment contamination from the charging region to the sterile filling region. The length of the plasma zone here also assures that possible local or chronological non-homogeneities of the plasma action on the surfaces of the container can be balanced out over the treatment time; the only requirement is that additional safety be taken into account.

A short processing time and efficiency in the treatment, since only the surface is treated, even makes it possible for plastics to be used as the container material. Previously, however, in most of the known devices, it was only possible for glass to be used as the container material due to the use of heat tunnels.

According to one embodiment, the chamber is provided with a transport apparatus inside it, which produces an essentially rotating motion of the container in the chamber during the transport from the arrival to the discharge. In this case, the plasma source, i.e. the device for generating the electromagnetic oscillations, is advantageously mounted outside the chamber and is separated from the inside of the chamber by a device that can execute a launch of the electromagnetic oscillations into the chamber in the container regions to be sterilized and can produce a pressure separation of the vacuum inside the chamber from the different pressure outside the chamber.

According to another advantageous embodiment, a transport apparatus is provided inside the chamber, which also produces an essentially rotating motion of the container in the chamber during the transport from the arrival to the discharge. In this instance, though, the at least one plasma source with the device for generating the electromagnetic oscillations is mounted inside the chamber and is separated from the inside of the chamber by a device. This device can execute a launch of electromagnetic oscillations into the chamber in the container regions to be sterilized. The at least one plasma source here can also be mounted directly inside one or more transport rollers for moving and transporting the containers.

The device that executes a launch of electromagnetic oscillations into the chamber in the container regions to be sterilized can advantageously be a layer of quartz, oxide-ceramic, or Teflon.

The at least one plasma source can, for example, be designed to generate electromagnetic oscillations in the microwave range. In this case, this plasma source is separated from the chamber by a microwave-permeable tube or plate. A microwave launch into the chamber is then executed by means of a slot aperture or a horn flare of a wave guide. On the other hand, in order to generate the electromagnetic oscillations, the at least one plasma source can also be provided with an electrode, which can execute a capacitive high-frequency launch by means of ion bombardment directed into the chamber. An advantageous device with a coil or a helical antenna can also be used, which can generate an inductive high-frequency launch into the chamber through a corresponding window in the device for separating the plasma source from the chamber. The window of the device for separating the plasma source from the chamber can also have a Faraday screen mounted on it, which can at least partially decouple the magnetic action from the electrical action of the radiated field.

According to a first embodiment, the transport of the containers with the apparatus according to the invention can be executed in a simple way in that during the transport in the chamber, the containers are arranged lying horizontally in the transport direction on at least two transport rollers, which are driven around a rotation axis that is also oriented horizontally in the transport direction. This allows the containers to be rotated past the launch region of the plasma source and transported at the same time.

In a second embodiment, during the transport in the chamber, the containers are arranged lying in a rotating tube and the at least one plasma source is disposed in the center of this tube or encompassing it from the outside. The tube is driven around a rotation axis that is oriented horizontally in the transport direction in such a way that the containers can be rotated past the launch region of the plasma source and transported at the same time.

According to a third embodiment, during the transport in the chamber, the containers are disposed on an inclined plane so that the containers roll around a rotation axis perpendicular to the transport direction and the containers can be rotated past the launch region of the plasma source and transported at the same time.

There is also a fourth advantageous embodiment in which, during the transport in the chamber, the containers are arranged lying on at least one roller, which has a worm gearing and is driven around a rotation axis oriented horizontally in the transport direction in such a way that the containers can be rotated past the launch region of the plasma source and transported at the same time. In a modification of this embodiment, vertically oriented rotating rollers can also be provided in the form of a worm drive and transport the containers in their middles. The containers here can be transported through the plasma in a particularly advantageous fashion, with their openings pointing downward.

A fifth embodiment makes it possible during the transport in the chamber, for the containers to be arranged lying on an apparatus, which can be moved in the transport direction and is comprised of rollers that can rotate perpendicular to the transport direction, between which the containers can be placed. The containers, which roll around a rotation axis perpendicular to the transport direction while the apparatus moves in the transport direction, are guided so that they can be rotated past the launch region of the plasma source and transported at the same time. The rotating motion of the rollers can be produced simply through the use of a chain drive or a gear drive on which the apparatus can be moved and with which the corresponding teeth of the rollers engage.

It is also advantageous if at least one additional plasma source is disposed under and/or next to the chamber and this additional plasma source can execute a sterilization of the transport apparatus and/or of containers that have fallen down from the transport apparatus. The method according to the invention can also be advantageously improved in that the sterilizing effectiveness of the plasma is determined by measuring the light emission, particularly with regard to the appearance, duration, and spectral components of the light.

BRIEF DESCRIPTION OF THE DRAWINGS

Exemplary embodiments of devices for executing the method according to the invention for sterilizing containers will be explained herein below, in conjunction with the drawings, in which:

FIG. 1 shows a schematic view of a device with a transport apparatus, which is disposed in a low-pressure or vacuum chamber and serves to convey the containers to be sterilized through the chamber, wherein a plasma is excited in the chamber, FIG. 2 shows a section through the transport apparatus according to FIG. 1, with two rollers, FIG. 6 shows a schematic view of an exemplary embodiment of a transport apparatus in which the containers are moved in a rotating tube and the plasma source is disposed in the center of this tube, FIG. 7 shows a cross section through the device according to FIG. 6, FIG. 8 shows a schematic view of an exemplary embodiment of a transport apparatus in which the containers move on an inclined plane, FIG. 9 shows a schematic view of an exemplary embodiment of a transport apparatus in which the containers are moved by means of a worm drive.

DESCRIPTION OF THE PREFERRED EMBODIMENTS

Figure 3:
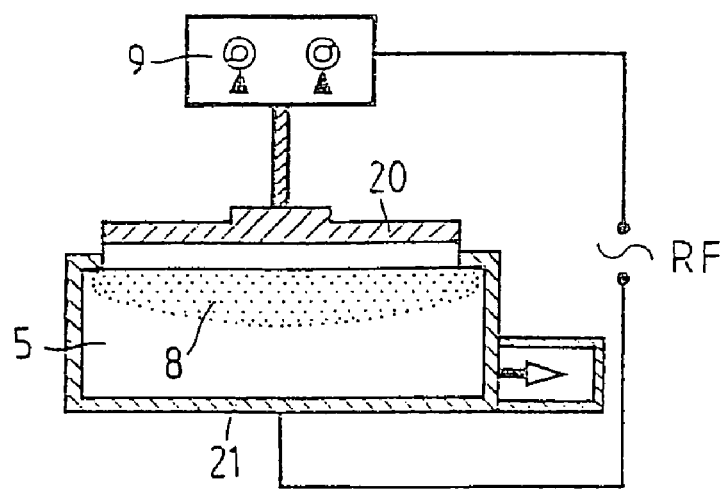
FIG. 3 shows a schematic wiring diagram for the excitation of plasma through the use of a high-frequency capacitive launch of the electromagnetic field.

FIG. 1 shows a first exemplary embodiment of a device 1, with which the containers 2 can be conveyed into a non-sterile region 3 of the device 1. The containers 2 are then transported by a mechanical apparatus, which is not explained in detail here, through a first port 4 into a low-pressure or vacuum chamber 5, and are moved therein by means of a transport apparatus, which will be described in detail below, toward a second port 6 in order to then be discharged into a sterile region 7 of the device 1, from which they can subsequently be withdrawn.

FIG. 1 shows a plasma 8 being generated in the chamber 5 by the field of a microwave transmitter serving as a plasma source; this is indicated here schematically by means of arrows 9. FIG. 2 shows the first embodiment of a transport apparatus for the example according to FIG. 1, in which the containers 2 are rotated by means of rollers or cylinders 10 and 11 while being transported from the port 4 to the port 6 so that all regions of the containers 2 are subjected to the plasma 8 in the same manner.

The two transport rollers 10 and 11 according to FIG. 2 can be slightly inclined in order to use the force of gravity to cover the distance between the port 4 and the port 6. The continuous rotation of the containers 2 minimizes the friction during the process of this movement.

One example of a plasma source is a line source, which guides the microwave radiation coaxially into the vacuum, in which a quartz tube defines the boundary between the vacuum and the internal normal pressure and on the interior, a concentrically disposed metal rod functions as an internal conductor. The plasma, which is excited on the outside of the quartz tube, serves as the external conductor. This principle can be utilized in a cascading fashion, with an array of the above-mentioned line sources, in order to generate plasma over an area. As a rule, the microwave device is operated at frequencies of 300 MHz to 30 GHz.

In addition, instead of the quartz tube, it is also possible to use a quartz plate. Instead of quartz as the tube or plate material, other microwave-permeable materials can also be used, for example oxide-ceramics or Teflon. It is also possible to launch the microwave radiation into the vacuum over an area by means of a slot aperture or a horn flare of a wave guide.

In this connection, with reference to the transport apparatus according to FIGS. 1 and 2, instead of the two prone, rotating transport rollers 10 and 11 made of an arbitrary material, it is also possible to use rotating quartz tubes with a copper rod on the inside, in which case the rollers 10 and 11 would be the actual plasma sources.

The principle operation of the plasma sterilization with the proposed device will be explained below.

The field intensity is at its greatest and can be excited with the greatest ease in the vicinity of the launch of the high-frequency or microwave radiation, in this instance the plasma source 9 according to FIG. 1. As an electric conductor, however, the plasma can also act as a shield by absorbing and dissipating radiation; this prevents or at least attenuates a further spreading of the radiation.

The minimal distance of the container 2 from the launch by the plasma source 9 in the exemplary embodiment described here prevents a so-called dense plasma from forming between the launch and the container 2. Therefore, a sufficient portion of the radiated power is also present inside the container 2 in order to excite a plasma 8 there as well. The distance between the wall of the container 2 and the launch can also be selected so that a plasma is present either only on the inside, or at least predominantly on the inside, only on the outside in the event of a large distance, or inside and outside at the same time. If a number of plasma sources 9 are used, then it is possible to produce a successive or simultaneous complete treatment of all wall regions of the container 2.

FIG. 3 shows a capacitive high-frequency launch (RF) for generating plasma for electromagnetic waves of approx. 10 kHz to 27 MHz. The launch occurs between an electrode 20 and an opposite electrode 21, which can be the housing of the vacuum chamber 5 connected to ground, in which the electrode 20 can assure a high ion bombardment if this electrode 20 has a smaller area in comparison to the significantly larger area of the opposite electrode 21.

Figure 4:
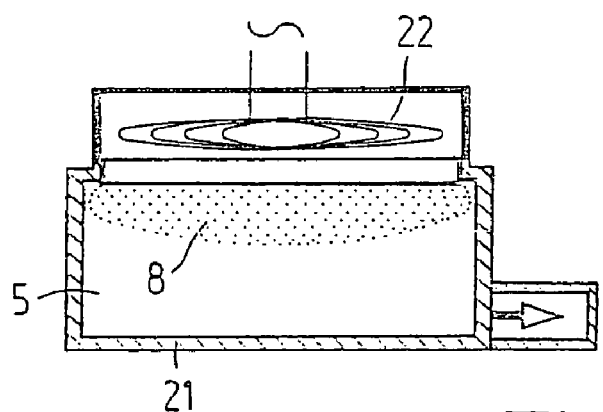
FIG. 4 shows a schematic wiring diagram for the excitation of plasma through the use of a high-frequency inductive launch of the electromagnetic field.

FIG. 4 shows an inductive high-frequency launch by means of a coil that functions as a helical antenna 22. This helical antenna 22 is exposed to atmospheric pressure and is mounted above a quartz or Teflon window in the chamber 5 that separates the interior of the chamber, which is under vacuum, from the exterior, which is under normal or atmospheric pressure.

Figure 5:
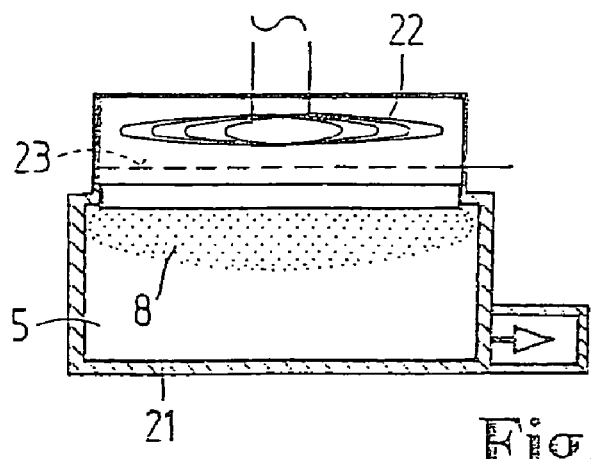
FIG. 5 shows a modification of the device according to FIG. 4, with a Faraday screen.

FIG. 5 shows an inductive high-frequency launch of the kind shown in FIG. 4, with an additional provision of a so-called Faraday shield 23, which contributes to the decoupling of the magnetic action from the electrical action of the radiated field.

In the exemplary embodiments below, still other possibilities are given for the transport of the containers 2 through the device 1 with simultaneous rotation.

In the exemplary embodiment according to FIGS. 6 and 7, the containers 2 are arranged inside an approximately horizontally oriented or slightly inclined rotating tube 24, the center of which contains, for example, a quartz tube 12 as described in conjunction with FIG. 2. Alternatively, one or more plasma sources can also be disposed encompassing the rotating tube 24, where in this case, the tube 24 is then made of quartz or Teflon.

FIG. 8 shows an exemplary embodiment in which the containers 2 roll on an inclined plane 25. The force of gravity causes the containers 2, which lie perpendicular to the transport direction 26, to rotate around their longitudinal axes.

In an exemplary embodiment according to FIG. 9, the two horizontally oriented rollers 27 and 28 (as compared to the rollers 10 and 11 in FIG. 2) have a thread or a thread-shaped zone let into them, with a higher friction coefficient than the rest of the roller surface and thus function as a worm drive so that the containers 2 can be transported in a definite manner from the port 4 to the port 6. It can also suffice to provide only one roller with such a thread structure and to use the second roller without a thread structure as a counterpart support, optionally with a low coefficient of friction on its surface.

The rollers with the threads 27 and 28 according to FIG. 9 can also be disposed vertically or almost vertically, for example when a third roller or a plate with a low surface friction coefficient is provided to assure that the containers 2 do not fall out of the guide mechanism. In this case, it is also possible for the containers 2 to be transported with their openings pointing downward. The plate can also be constituted by the launching window of the electric field, which is exerted in order to excite a plasma in the vacuum.

Figure 10:
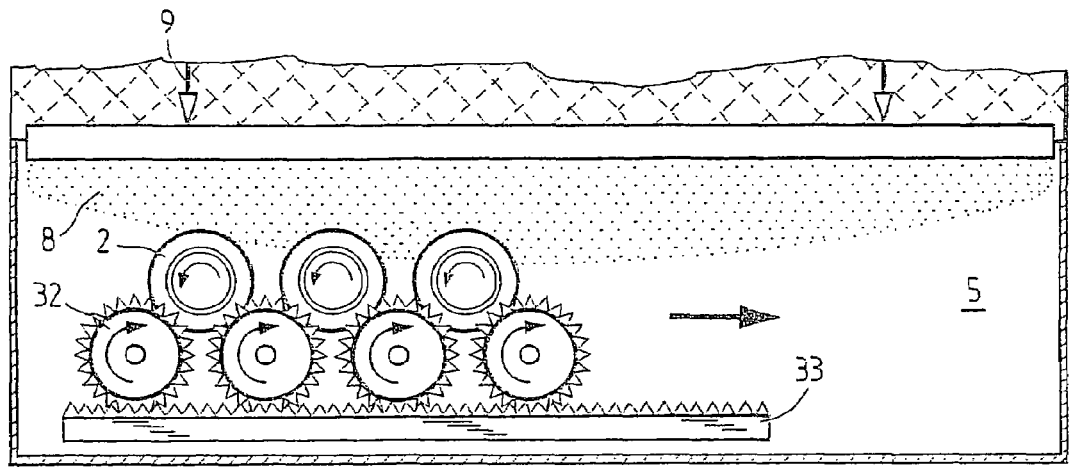
FIG. 10 shows a schematic view of an exemplary embodiment of a transport apparatus in which the containers are moved by means of a chain transport apparatus.
Figure 11:
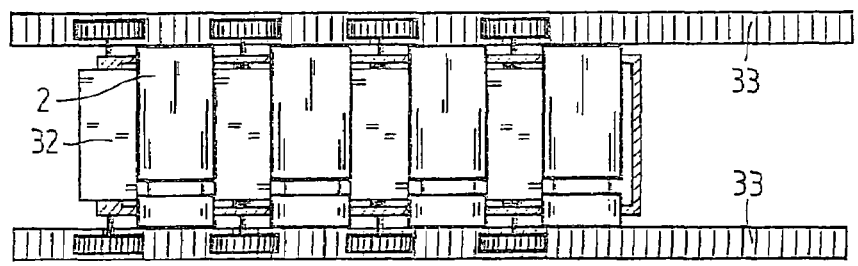
FIG. 11 shows a top view of the chain transport apparatus according to FIG. 10.

According to FIGS. 10 and 11, the containers can also be transported on rollers 32, which are driven on a chain 33 by means of a gear drive. The chain links are designed so that the containers 2 disposed on them are set into rotation around their longitudinal axes.

Figure 12:
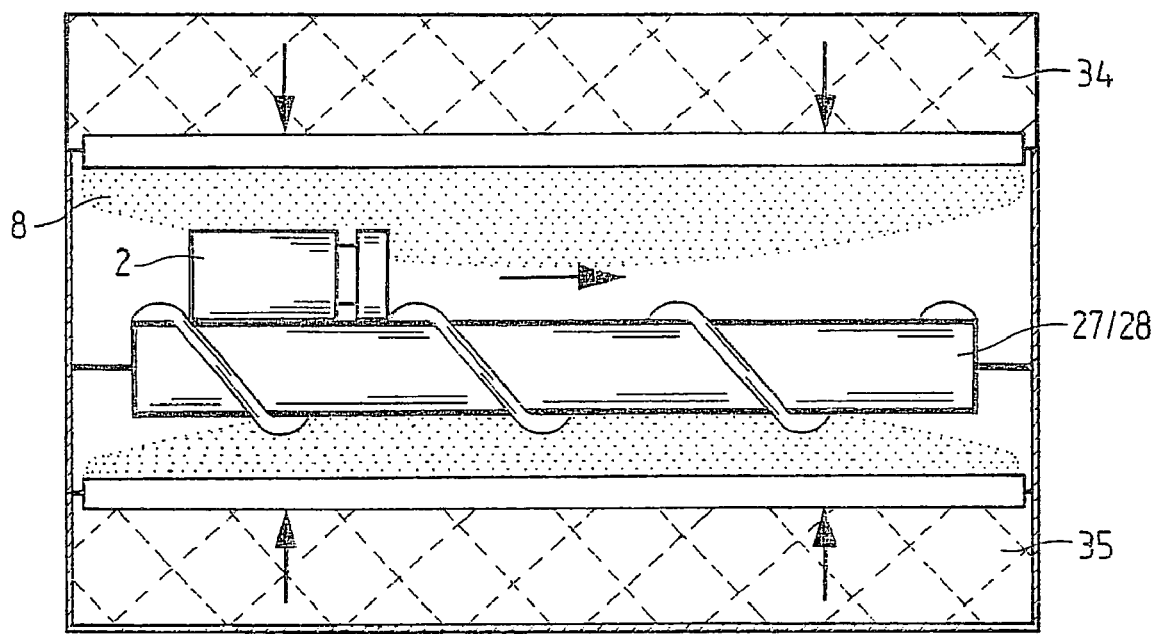
FIG. 12 shows a schematic view of a device with one of the transport apparatuses mentioned above, in which a plasma is excited in the chamber by means of two plasma sources disposed opposite each other.

In order to achieve the sterilization of the above-described transport apparatuses in an even more reliable fashion, according to FIG. 12, one or more additional plasma sources 34, 35 can also be placed under or next to the transport apparatus, which in this case is the one according to FIG. 9. The plasma source 35 under the transport apparatus could also be used to sterilize containers 2 that may have fallen down from the treatment region or other articles, parts, or particles.

The foregoing relates to preferred exemplary embodiments of the invention, it being understood that other variants and embodiments thereof are possible within the spirit and scope of the invention, the latter being defined by the appended claims.

We claim:

1. A method for sterilizing containers (2), the method comprising
    executing a plasma treatment in at least one process step in a chamber (5) through excitation of an electromagnetic oscillation by an oscillating device (a) so that the plasma (8) is excited in a vacuum in the vicinity of the container (2) regions to be sterilized, and
    moving the container (2) regions to be sterilized closer to the oscillation-generating device (9) in the chamber (5) between the arrival (4) and discharge (6), and continuously moving the container (2) and/or the oscillation-generating device (9) while the plasma is excited for one or more predetermined time intervals in such a way that a plasma (8) is excited in regions inside and/or outside the container.

2. The method according to claim 1, wherein
    the plasma treatment is a sterilization and/or a de-pyrogenization.

3. The method according to claim 2, further comprising
    determining the sterilizing effectiveness of the plasma (8) by measuring the light emission, particularly with regard to the appearance, duration, and spectral components of the light.

4. The method according to claim 1, further comprising
    determining the sterilizing effectiveness of the plasma (8) by measuring the light emission, particularly with regard to the appearance, duration, and spectral components of the light.

5. A device for executing the method according to claim 1, further comprising
    a transport apparatus inside the chamber (5), which transport apparatus produces an essentially rotating motion of the container (2) in the chamber (5) during the transport from the arrival (4) to the discharge (6), and wherein
    the plasma source (9) with the device for generating the electromagnetic oscillations is mounted completely outside the chamber (5) and is separated from the inside of the chamber (5) by a device that can execute a launch of the electromagnetic oscillations into the chamber (5) in the container (2) regions to be sterilized and this can be used to produce a pressure separation of the vacuum inside the chamber (5) from the different pressure outside the chamber (5).

6. The device according to claim 5, wherein
    the at least one plasma source for exciting the electromagnetic oscillations in the microwave range is separated from the chamber by a microwave-permeable tube or plate, and wherein
    it is possible to launch the microwave radiation into the chamber by means of a slot aperture or a horn flare of a wave guide.

7. The device according to claim 5, wherein
    the at least one plasma source for exciting the electromagnetic oscillations is an electrode, which can produce a capacitive high-frequency launch by means of ion bombardment directed into the chamber.

8. The device according to claim 5, wherein
    the at least one plasma source for exciting the electromagnetic oscillations is a coil, which can produce an inductive high-frequency launch into the chamber through a corresponding window in the device for separating the plasma source from the chamber.

9. The device according to claim 8, further comprising
    a Faraday screen mounted on the window of the device for separating the plasma source from the chamber, which Faraday screen can at least partially decouple the magnetic action from the electrical action of the radiated field.

10. The device according to claim 5, wherein
    during the transport in the chamber, the containers are arranged lying horizontally in the transport direction on at least two transport rollers that are driven around a rotation axis, which is also oriented horizontally in the transport direction, in such a way that the containers can be rotated past the launch region of the plasma source and transported at the same time.

11. The device according to claim 5, wherein
    during the transport in the chamber, the containers are arranged lying in a rotating tube and the at least one plasma source is disposed in the center of this tube or encompassing it from the outside and the tube is driven around a rotation axis that is oriented horizontally in the transport direction, in such a way that the containers can be rotated past the launch region of the plasma source and transported at the same time.

12. The device according to claim 5, wherein
during the transport in the chamber, the containers are arranged lying on an inclined plane so that they roll around a rotation axis perpendicular to the transport direction, thus allowing the containers to be rotated past the launch region of the plasma source and transported at the same time.

13. The device according to claim 5, wherein
during the transport in the chamber, the containers are arranged lying on or against at least one roller with a worm gear or another high friction thread-shaped structure; this roller is driven around a rotation axis perpendicular to the transport direction in such a way that the containers can be rotated past the launch region of the plasma source and transported at the same time.

14. The device according to claim 5, wherein
during the transport in the chamber, the containers are arranged lying on an apparatus that can be moved in the transport direction and is comprised of rollers, which can be rotated perpendicular to the transport direction and between which the containers rest, and that
during the movement of the apparatus in the transport direction, the containers roll on a rotation axis perpendicular to the transport direction so that the containers can be rotated past the launch region of the plasma source and transported at the same time.

15. The device according to claim 14, further comprising
a chain or gear drive producing the rotating motion of the rollers, on which chain or gear driver the apparatus can be moved and which is engaged by corresponding teeth of the rollers.

16. The device according to claim 5, further comprising
at least one additional plasma source disposed under and/or to the side of the chamber, which additional plasma source can execute a sterilization of the transport apparatus and/or of containers (2) that have fallen down from the transport apparatus.

17. A device for executing the method according to claim 1, further comprising
a transport apparatus inside the chamber (5) which produces an essentially rotating motion of the container (2) in the chamber (5) during the transport from the arrival (4) to the discharge (6), and wherein
the at least one plasma source (9) with the device for generating the electromagnetic oscillations is mounted inside the chamber (5), which is once again divided and this division separates the plasma source (9) from the treatment area of the chamber (5) so that despite the presence of an electromagnetic field, it is possible to execute a launch into the container(s) (2).

18. The device according to claim 17, wherein
the at least one plasma source is mounted inside one or more transport rollers (10, 11) for moving and transporting the containers.

19. The device according to claim 18, wherein
the device that executes a launch of electromagnetic oscillations into the chamber in the container regions to be sterilized is a layer or other formation made of quartz, oxide-ceramic, or Teflon.

20. The device according to claim 18, wherein
the at least one plasma source for exciting the electromagnetic oscillations in the microwave range is separated from the chamber by a microwave-permeable tube or plate, and wherein
it is possible to launch the microwave radiation into the chamber by means of a slot aperture or a horn flare of a wave guide.

21. The device according to claim 17, wherein
the device that executes a launch of electromagnetic oscillations into the chamber in the container regions to be sterilized is a layer or other formation made of quartz, oxide-ceramic, or Teflon.

22. The device according to claim 21, wherein
the at least one plasma source for exciting the electromagnetic oscillations in the microwave range is separated from the chamber by a microwave-permeable tube or plate, and wherein
it is possible to launch the microwave radiation into the chamber by means of a slot aperture or a horn flare of a wave guide.

23. The device according to claim 17, wherein
the at least one plasma source for exciting the electromagnetic oscillations in the microwave range is separated from the chamber by a microwave-permeable tube or plate, and wherein
it is possible to launch the microwave radiation into the chamber by means of a slot aperture or a horn flare of a wave guide.

* * * * *